(12) United States Patent
Bottje et al.

(10) Patent No.: US 10,842,858 B2
(45) Date of Patent: *Nov. 24, 2020

(54) COMPOSITIONS AND METHODS OF ENHANCING IMMUNE RESPONSES TO EIMERIA

(71) Applicants: THE BOARD OF TRUSTEES OF THE UNIVERSITY OF ARKANSAS, Little Rock, AR (US); THE TEXAS A&M UNIVERSITY SYSTEM, College Station, TX (US)

(72) Inventors: Walter Bottje, Fayetteville, AR (US); Billy Hargis, Fayetteville, AR (US); Luc Berghman, College Station, TX (US); Young Min Kwon, West Fork, AR (US); Kimberly Cole, Raymond, OH (US); Mandy Cox, Fayetteville, AR (US); Sherryll Layton, Rogers, AR (US); Saeed El-Ashram, Kafrelsheikh (EG); John Barta, Guelph (CA); Guillermo Tellez, Fayetteville, AR (US)

(73) Assignees: THE BOARD OF TRUSTEES OF THE UNIVERSITY OF ARKANSAS, Little Rock, AR (US); THE TEXAS A&M UNIVERSITY SYSTEM, College Station, TX (US); THE UNIVERSITY OF GUELPH (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/028,599

(22) Filed: Jul. 6, 2018

(65) Prior Publication Data
US 2018/0333474 A1 Nov. 22, 2018

Related U.S. Application Data

(63) Continuation of application No. 14/623,050, filed on Feb. 16, 2015, now Pat. No. 10,016,493, which is a continuation of application No. 12/740,608, filed as application No. PCT/US2008/082254 on Nov. 3, 2008, now Pat. No. 8,956,849.

(60) Provisional application No. 60/984,612, filed on Nov. 1, 2007.

(51) Int. Cl.
| | | |
|---|---|---|
| *A61K 39/002* | (2006.01) | |
| *C07K 14/455* | (2006.01) | |
| *C07K 14/705* | (2006.01) | |
| *A61K 39/00* | (2006.01) | |

(52) U.S. Cl.
CPC .......... *A61K 39/002* (2013.01); *C07K 14/455* (2013.01); *C07K 14/70575* (2013.01); *A61K 2039/523* (2013.01); *A61K 2039/53* (2013.01); *C07K 2319/03* (2013.01); *Y02A 50/30* (2018.01)

(58) Field of Classification Search
None
See application file for complete search history.

(56) References Cited

U.S. PATENT DOCUMENTS

| | | |
|---|---|---|
| 5,540,926 A | 7/1996 | Aruffo |
| 5,565,321 A | 10/1996 | Spriggs et al. |
| 5,683,700 A | 11/1997 | Charles et al. |
| 5,716,805 A | 2/1998 | Srinivasan et al. |
| 5,747,309 A | 5/1998 | Allan et al. |
| 5,817,516 A | 10/1998 | Kehry |
| 5,961,974 A | 10/1999 | Armitage et al. |
| 5,962,406 A | 10/1999 | Armitage et al. |
| 5,981,724 A | 11/1999 | Armitage et al. |
| 6,087,329 A | 7/2000 | Armitage et al. |
| 6,190,669 B1 | 2/2001 | Noriega et al. |
| 6,264,951 B1 | 7/2001 | Armitage et al. |
| 6,306,387 B1 | 10/2001 | Galan |
| 6,410,711 B1 | 6/2002 | Armitage et al. |
| 6,479,258 B1 | 11/2002 | Short |
| 6,713,279 B1 | 3/2004 | Short |
| 6,902,906 B1 | 6/2005 | Chatfield |
| 6,923,957 B2 | 8/2005 | Lowery et al. |
| 6,923,958 B2 | 8/2005 | Xiang et al. |
| 6,936,425 B1 | 8/2005 | Hensel et al. |
| 6,969,609 B1 | 11/2005 | Schlom et al. |
| 7,087,573 B1 | 8/2006 | Lazarus et al. |
| 7,118,751 B1 | 10/2006 | Ledbetter et al. |
| 7,238,499 B2 | 7/2007 | Reddy |
| 7,332,298 B2 | 2/2008 | Kornbluth |
| 7,371,392 B2 | 5/2008 | Tripp et al. |

(Continued)

FOREIGN PATENT DOCUMENTS

| | | |
|---|---|---|
| WO | WO 1993/008207 | 4/1993 |
| WO | WO 1995/014487 | 6/1995 |

(Continued)

OTHER PUBLICATIONS

Kimani et al, Molecular Therapy, Nov. 2014, Nov. 22, 1992-2003. advance online publication: Jul. 29, 2014. (Year: 2014).*

(Continued)

*Primary Examiner* — Nita M. Minnifield
(74) *Attorney, Agent, or Firm* — Quarles & Brady LLP

(57) ABSTRACT

Vaccines comprising TRAP polypeptides and *Salmonella enteritidis* vectors comprising TRAP polypeptides are provided. The vaccines may also include a CD154 polypeptide capable of binding to CD40. Also provided are methods of enhancing an immune response against Apicomplexan parasites and methods of reducing morbidity associated with infection with Apicomplexan parasites.

22 Claims, 3 Drawing Sheets

Specification includes a Sequence Listing.

(56) References Cited

U.S. PATENT DOCUMENTS

| | | | |
|---|---|---|---|
| 7,405,270 B2 | 7/2008 | Armitage et al. | |
| 7,423,137 B2 | 9/2008 | Belli et al. | |
| 7,462,707 B1 | 12/2008 | Witcombe | |
| 7,495,090 B2 | 2/2009 | Prussak et al. | |
| 7,803,765 B2 | 9/2010 | Watt et al. | |
| 7,842,501 B2 | 11/2010 | Cai et al. | |
| 7,928,213 B2 | 4/2011 | Prussak et al. | |
| 7,968,695 B2 | 5/2011 | Belli et al. | |
| 8,142,771 B2 | 5/2012 | Suo et al. | |
| 8,316,310 B2 | 11/2012 | Bernard et al. | |
| 8,604,178 B2 | 12/2013 | Bottje et al. | |
| 8,956,618 B2 * | 2/2015 | Berghman | A61K 39/12 424/184.1 |
| 8,956,849 B2 * | 2/2015 | Bottje | C07K 14/455 435/235.1 |
| 9,125,854 B2 | 9/2015 | Bottje et al. | |
| 9,226,957 B2 * | 1/2016 | Bottje | A61K 39/0275 |
| 9,603,915 B2 * | 3/2017 | Barta | A61K 39/012 |
| 9,884,099 B2 * | 2/2018 | Barta | A61K 39/012 |
| 9,913,893 B2 * | 3/2018 | Berghman | A61K 39/12 |
| 10,000,550 B2 * | 6/2018 | Hill | C07K 14/525 |
| 10,000,553 B2 * | 6/2018 | Coyle | C07K 14/78 |
| 10,004,798 B2 * | 6/2018 | Bottje | A61K 39/0275 |
| 10,023,645 B1 * | 7/2018 | Cohen | C07K 16/2818 |
| 10,118,953 B2 * | 11/2018 | Hill | C07K 14/525 |
| 10,137,206 B2 * | 11/2018 | Angel | A61K 48/0066 |
| 10,328,137 B2 * | 6/2019 | Barta | A61K 39/012 |
| 10,328,146 B2 * | 6/2019 | Ertl | A61K 39/245 |
| 10,376,571 B2 * | 8/2019 | Bielke | |
| 10,407,491 B2 * | 9/2019 | Mwangi | C07K 16/081 |
| 2001/0021386 A1 | 9/2001 | Nuijten et al. | |
| 2003/0045492 A1 | 3/2003 | Tang et al. | |
| 2003/0091548 A1 | 5/2003 | Young et al. | |
| 2003/0119149 A1 | 6/2003 | Reddy | |
| 2003/0165538 A1 | 9/2003 | Goldman et al. | |
| 2004/0006006 A9 | 1/2004 | Armitage et al. | |
| 2004/0047873 A1 | 3/2004 | Al-Shamkhani et al. | |
| 2004/0203039 A1 | 10/2004 | Hensel et al. | |
| 2005/0033042 A1 | 2/2005 | Belli et al. | |
| 2005/0181994 A1 | 8/2005 | Chamberlain et al. | |
| 2005/0226888 A1 | 10/2005 | Deisseroth et al. | |
| 2006/0014248 A1 | 1/2006 | Marshall et al. | |
| 2006/0078994 A1 | 4/2006 | Healey et al. | |
| 2006/0233829 A1 | 10/2006 | Curtiss | |
| 2006/0286074 A1 | 12/2006 | Tang et al. | |
| 2007/0025982 A1 | 2/2007 | Ledbetter et al. | |
| 2007/0031832 A1 | 2/2007 | Watt et al. | |
| 2007/0082400 A1 | 4/2007 | Healey et al. | |
| 2007/0128223 A1 | 6/2007 | Tang et al. | |
| 2007/0237779 A1 | 10/2007 | Ledbetter et al. | |
| 2009/0004194 A1 | 1/2009 | Kedl | |
| 2009/0196888 A1 | 8/2009 | Belli et al. | |
| 2009/0324644 A1 | 12/2009 | Ramos et al. | |
| 2010/0047231 A1 | 2/2010 | Zabaleta Azpiroz et al. | |
| 2010/0112002 A1 | 5/2010 | Lien et al. | |
| 2010/0150958 A1 * | 6/2010 | Sheppard | A61K 39/012 424/201.1 |
| 2010/0163668 A1 | 7/2010 | Nannoni et al. | |
| 2010/0291109 A1 | 11/2010 | Kedl | |
| 2010/0292309 A1 | 11/2010 | Vile et al. | |
| 2011/0111015 A1 * | 5/2011 | Bottje | C07K 14/455 424/450 |
| 2011/0159026 A1 | 6/2011 | Bottje et al. | |
| 2014/0093534 A1 * | 4/2014 | Bottje | A61K 39/0275 424/200.1 |
| 2015/0150958 A1 | 6/2015 | Pillich | |
| 2015/0190500 A1 * | 7/2015 | Berghman | A61K 39/12 424/186.1 |
| 2015/0216954 A1 * | 8/2015 | Bottje | C07K 14/455 424/185.1 |
| 2016/0000895 A1 * | 1/2016 | Barta | A61K 39/012 424/191.1 |
| 2016/0114025 A1 | 4/2016 | Bottje | |
| 2017/0182136 A1 * | 6/2017 | Barta | A61K 39/012 |
| 2017/0196971 A1 * | 7/2017 | Berghman | A61K 9/0019 |
| 2018/0028686 A1 * | 2/2018 | Brinker | C12N 15/8206 |
| 2018/0169198 A1 * | 6/2018 | Barta | A61K 39/012 |
| 2018/0333474 A1 * | 11/2018 | Bottje | C07K 14/455 |
| 2019/0112380 A1 * | 4/2019 | Chaudhary | C07K 16/2803 |

FOREIGN PATENT DOCUMENTS

| | | | |
|---|---|---|---|
| WO | WO 1996/026735 | 9/1996 | |
| WO | WO 1996/040918 | 12/1996 | |
| WO | WO 1999/027948 | 6/1999 | |
| WO | WO 1999/032138 | 7/1999 | |
| WO | WO 2000/063395 | 10/2000 | |
| WO | WO 2000/063405 | 10/2000 | |
| WO | WO 2001/042298 | 6/2001 | |
| WO | WO 2001/056602 | 8/2001 | |
| WO | WO 2002/036769 | 5/2002 | |
| WO | WO 2002/092773 | 11/2002 | |
| WO | WO 2003/004683 | 1/2003 | |
| WO | WO 2003/004684 | 1/2003 | |
| WO | WO 2003/026691 | 4/2003 | |
| WO | WO 2003/099340 | 12/2003 | |
| WO | WO 2004/009615 | 1/2004 | |
| WO | WO 2005/035570 | 4/2005 | |
| WO | WO 2005/058950 | 6/2005 | |
| WO | WO 2005/113598 | 12/2005 | |
| WO | WO 2006/042177 | 4/2006 | |
| WO | WO 2006/105972 | 10/2006 | |
| WO | WO 2007/042583 | 4/2007 | |
| WO | WO 2007/054658 | 5/2007 | |
| WO | WO 2007/056266 | 5/2007 | |
| WO | WO 2007/103048 | 9/2007 | |
| WO | WO 2007/117682 | 10/2007 | |
| WO | WO 2008/036675 | 3/2008 | |
| WO | WO 2008/109825 | 9/2008 | |
| WO | WO 2009/059018 | 5/2009 | |
| WO | WO 2009/059298 | 5/2009 | |
| WO | WO-2009059298 A2 * | 5/2009 | C07K 14/455 |
| WO | WO 2014/070709 | 5/2014 | |
| WO | WO-2014127185 A1 * | 8/2014 | A61K 39/002 |
| WO | WO-2015187969 A2 * | 12/2015 | |

OTHER PUBLICATIONS

Manoj, S. et al., "Targeting with Bovine CD154 enhances humoral immune responses induced by a DNA vaccine in sheep," (2003) Journal of Immunology 170:989-996.

Mauriello, E.M.F. et al., "Display of heterologous antigens on the Bacillus subtilis spore coat using CotC as a fusion partner," (2004) Vaccine 22(9-10):1177-1187.

McConkey, S.J. et al., "Enhanced T-cell immunogenicity of plasmid DNA vaccines boosted by recombinant modified vaccinia virus Ankara in humans," (2003) Nature Medicine 9(6):729-735.

Mendoza, R.B. et al., "Cutting edge: Immunostimulatory effects of a plasmid expressing CD40 ligand (CD154) on gene immunization," Journal of Immunology (1997) 159(12):5777-5781.

Miga, a. et al., "The role of CD40-CD154 interactions in the regulation of cell mediated immunity," Immunol. Invest. (2000) 29:111-114.

Mohamadzadeh, M. et al., "Targeting mucosal dendritic cells with microbial antigens from probiotic lactic acid bacteria," Expert Rev. Vaccines (2008) 7(2):163-174.

Moyle, P.M. et al., "Mucosal immunisation: adjuvants and delivery systems," Curr. Drug Deliv. (2004) 1(4):385-396.

Nakajima, a. et al., "Antitumor effect of CD40 ligand: Elicitation of local and systemic antitumor responses by IL-12 and B7," (1998) Journal of Immunology 161:1901-1907.

National Center for Biotechnology Information [http://www.ncbi.nlm.nih.gov/protein/74811618?].

O'Callaghan, D. et al., "Immunogenicity of foreign peptide epitopes expressed in bacterial envelope proteins," Research in Microbiology (1990) 141:963-969.

Ochoa-Reparaz, J. et al., "Humoral immune reponse in hens naturally infected with *Salmonella enteritidis* against outer membrane proteins and other surface structural antigens," (2004) Vet. Res. 35:291-298.

(56) References Cited

OTHER PUBLICATIONS

Pasetti, M. et al., "Animal models paving the way for clinical trials of attenuated *Salmonella enterica* servoar Typhi live oral vaccines and live vectors," Vaccine (2003) 21:401-418.
Patarroyo, M. et al., "Induction of protective immunity against experimental infection with malaria using synthetic peptides," (1987) Nature 328(6131):629-632.
Pogonka, T. et al., "A single dose of recombinant *Salmonella typhimurium* induces specific humoral immune responses against heterologous Eimeria tenella antigens in chicken," International Journal of Parasitology (2003) 33 :81-88.
Rabsch, W. et al., "Competitive exclusion of *Salmonella enteritidis* by *Salmonella gallinarum* in poultry," Emerging Inf. Diseases (2000) 6(5):443-448.
Rudinger, J. et al., "Characteristics of the amino acids as components of a peptide hormone sequence" (1976) Peptide Hormones Biol. Council 5-7.
Russmann, H. et al., "Delivery of epitopes by the *Salmonella* type III secretion system for vaccine development," Science (1998) 281(5376):565-568.
Schneider, J. et al., "A prime-boost immunisation regimen using DNA followed by recombinant modified vaccinia virus Ankara induces strong cellular immune responses against the Plasmodium falciparum TRAP antigen in chimpanzees," Vaccine (2001) 19(32): 4595-4602.
Seo, et al., "Mucosal humoral immunity to experimental *Salmonella enteritidis* infection in the chicken crop," Avian Diseases (2002) 46(4):1015-1020; p. 1018 fig 2a.
Shivaramaiah, S. et al., "Development and evaluation of an ΔaroA I ΔhtrA *Salmonella enteritidis* Vector Expressing Eimeria maxima TRAP Family Protein EmTFP250 with CD 154 (CD 40L) as Candidate VAccines against Coccidiosis in Broilers," International Journal of Poultry Science (2010) 9(11): 1031-1037.
Sizemore, D.R. et al., "Live, attenuated *Salmonella typhimurium* vectoring Campylobacter antigens," Vaccine (2006) 24(18):3793-3803.
Skolnick, J. et al., ""From genes to protein structure and function: novel applications of computational approaches in the genomic era,"" Trends in Biotechnol. (2000) 18(1):34-39.
Smith, et al., ""Maternal transmission of immunity to Eimeria maxima: western blot analysis of protective antibodies induced by infection,"" Infect. Immun. (1994) 62:1348-1357.
Su, G.F. et al., "Construction of stable LamB-Shiga toxin B subunit hybrids: analysis of expression in *Salmonella typhimurium* aroA strains and stimulation of B subunit-specific mucosal and serum antibody responses," Infect Immun (1992) 60(8):3345-3359.
Swayne, D.E., "Vaccines for List A poultry diseases: emphasis on avian influenza," Dev. Biol. (2003) 114:201-212.
Tregaskes, C.A. et al., "Conservation of biological properties of the CD40 ligand, CD154 in a non-mammalian vertebrate," Dev. Comp. Immunol. (2005) 29:361-374.
Vega, M.L. et al., "A *Salmonella typhi* OmpC fusion protein expressing the CD154 Trp140-Ser149 amino acid strand binds CD40 and activates a lymphoma B-cell line," Immunol. (2003) 110:206-216.
Verjans, G.M. et al., "Intracellular processing and presentation of T cell epitopes, expressed by recombinant *Escherichia coli* and *Salmonella typhimurium*, to human T cells," Eur J Immunol (1995) 25(2):405-410.
Vermeulen, A.N., "Progress in recombinant vaccine development against coccidiosis a review and prospects into the next millennium," International Journal of Parasitology (1998) 28:1121-1130.
Vierira-Pinto, M. et al.., "Occurrence of *Salmonella* in the ileum, ileocolic lymph nodes, tonsils, mandibular lymph nodes and carcasses of pigs slaughtered for consumption," J Vet Med B Infection Dis Vet Public Health (2005) 52(10):476-81.
Wallach, M. et al., "Maternal immunization with gametocyte antigens as a means of providing protective immunity against Emeria maxima in chickens," Infection and Immunity, (1992) 60(5):2036-2039.

Wang, J. et al., "Immunogenicity of viral B-cell epitopes inserted into two surface loops of the *Escherichia coli* K12 LamB protein and expressed in an attenuated aroA strain of *Salmonella typhimurium*," Vaccine (1999) 17(1):1-12.
Webster et al., "Safety of recombinant fowlpox strain FP9 and modified vacciniavirus Ankara vaccines against liver-stage P. falciparum malaria in non-immune volunteers," Vaccine (2006) 24:3026-3034.
Witcombe, D.M. et al., "Eimeria maxima TRAP family protein EmTFP250: subcellular localisation and induction of immune responses by immunization with a recombinant C-terminal derivative," Int. Jour. Parisitology.(2004) 34(7):861-872; abstract, p. 862 fig 1.
Witcombe, D.M. et al., "Molecular characterisation of EmTFP250: A novel member of the TRAP protein family in Eimeria maxima," International Journal of Parasitology (2003) 33(7):691-702.
Xu, Y. et al., "The role of CD4O-CD154 interaction in cell immunoregulation," J. Biomed. Sci. (2004) 11:426-438.
Yang, G. et al, Eimeria Tenella: Construction of a Recombinant Fowlpox Virus Expressing Rhomboid Gene and its Protective Efficacy Against Homologous Infection. Exp Parasitol, Dec. 25, 2007, vol. 119, No. 1, pp. 30-36.
International Search Report and Written Opinion for Application No. PCT/US08/81813 dated May 12, 2009 (13 pages).
International Search Report and Written Opinion for Application No. PCT/US08/082254 dated Jun. 17, 2009 (12 pages).
International Search Report and Written Opinion for International Patent Application No. PCT/US2011/022062 dated Mar. 29, 2011 (16 pages).
Extended European Search Report for EP Patent Application No. 08843740.5 dated May 3, 2011 (15 pages).
Office Action for Philippine Patent Application No. 1-2009-500491 dated May 30, 2012 (2 pages).
Examination Report for European Patent Application No. 08 843 740.5 dated Aug. 17, 2012 (6 pages).
First Office Action (translation of pertinent portions) for Chinese Patent Application No. 200880116875.0 (3 pages).
Office Action for Chinese Patent Application No. 200780037288.8 dated Dec. 25, 2012 (4 pages) (no refs).
Examination Report for European Patent Application No. 08 832 781.2 dated Jan. 9, 2013 (5 pages) (no new refs).
Office Action for U.S. Appl. No. 12/740,608 dated Aug. 22, 2013 (24 pages).
Office Action of U.S. Appl. No. 12/740,608 dated Jun. 16, 2014 (10 pages).
Office Action for Divisional U.S. Appl. No. 14/623,050 dated Jun. 28, 2016.
Office Action for Divisional U.S. Appl. No. 14/623,050 dated Dec. 15, 2016.
Office Action for Divisional U.S. Appl. No. 14/623,050 dated May 18, 2017.
Office Action for Divisional U.S. Appl. No. 14/623,050 dated Sep. 8, 2017.
Office Action for Divisional U.S. Appl. No. 14/623,050 dated Jan. 11, 2018.
Agterberg, M. et al., "Outer membrane protein PhoE as a carrier for the exposure of foreign antigenic determinants at the bacterial cell surface," Antonie Van Leeuwenhoek (1991) 59(4):249-262.
Al-Ramadi, B. K. et al., "Induction of innate immunity by IL-2 expressing *Salmonella* confers protection against letal challenge," Mol. Immunol. (2003) 39:763-770.
Al-Ramadi, B. K. et al., "Influence of vector-encoded cytokines on anti-*Salmonella* immunity: divergent effects of interleukin-2 and tumor necrosis factor alpha," Infect. Immun. (2001) 69:3960-3988.
Al-Ramadi et al., "CD154 is essential for Protective Immunity in Experimental *Salmonella* Infection: Evidence for a Dual Role in Innate and Adaptive Immune Responses" (2006) J Immunol 176: 496-506.
Babu, U., et al., "*Salmonella enteritidis* clearance and immune responses in chickens following *Salmonella* vaccination and challenge," Vet. Immunol. Immunopathol. (2004)101:251-257.
Barr, T.A. et al., "A potent adjuvant effect of CD40 antibody attached to antigen," Immunology (2003) 109:87-92.

(56) References Cited

OTHER PUBLICATIONS

Barrow, P. A., et al., "Reduction in faecal excretion of *Salmonella typhimurium* strain F98 in chickens vaccinated with live and killed *S. typhimurium* organisms," Epidemiol. Infect. (1990) 104:413-426.
Blomfield, I.C. et al., "Allelic exchange in *Escherichia coli* using the Bacillus subtilis sacB gene and a temperature-sensitive pSC101 replicon," Mol Microbiol (1991) 5(6):1447-1457.
Brossier, F. et al., "A spatially localized rhomboid protease cleaves cell surface adhesins essential for invasion by Toxoplasma," Proceedings of the National Academy of Sciences (2005) 102(11):4146-4151.
Buckley, A.M. et al., "Evaluation of live-attenuated *Salmonella* vaccines expressing Campylobacter antigens for control of C. jejuni in poultry," (2010) Vaccine 28(4):1094-1105.
Charbit, A. et al., "Probing the topology of a bacterial membrane protein by genetic insertion of a foreign epitope; expression at the cell surface," EMBO J (1986) 5(11):3029-3037.
Charbit, A. et al., "Versatility of a vector for expressing foreign polypeptides at the surface of gram-negative bacteria," Gene (1988) 70(1):181-189.
Chatfield et al., "The development of oral vaccines based on live attenuated *Salmonella* strains," FEMS Immunol. Med. Microbiol. (1993) 7:1-7.
Chothia, C. et al., "The relation between the divergence of sequence and structure in proteins," The EMBO Journal (1986) 5(4):823-826.
Cole, K. et al., "Evaluation of a novel recombinant salmonella vaccine vector for avian influenza," Poultry Science (2007) 86(Supp. 1):585-586.
Cox, M.M. et al., "Scarless and site-directed mutagenesis in *Salmonella enteritidis* chromosome," BMC Biotech. (2007) 7(59):10 pages.
Danforth, H.D. et al., "Genetically engineered antigen confers partial protection against avian coccidial parasites," (1989) Poultry Science 68:1643-1652.
Du, A. et al., "Efficacy of a DNA vaccine delivered in attenuated *Salmonella typhimurium* against Eimeria tenella infection in chickens," International Journal of Parasitology (2005) 35:777-785.
Ellis, R.W., "New technologies for making vaccines," (1988) Vaccines, Chapter 29:568-574.
Faham, A. et al., "Liposomal Ag engrafted with peptides of sequence derived from HMGB1 induce potent Ag-specific and anti-tumour immunity," (2009) 27(42):5846-5854.
Farnell, M.B. et al., "Upregulation of oxidative burst and degranulation in chicken heterophils stimulated with probiotic bacteria," Poult. Sci. (2006) 85:1900-1906.
Fecteau, J.F. et al., "CD40 Stimulation of Human Peripheral B Lymphocytes: Distinct Response from Naïve and Memory Cells," J Immunol (2003) 171:4621-4629.
Fernandez-Cabezudo et al., "Evidence for the requirement for CD40-CD154 interactions in resistance to infections with attenuated *Salmonella*," J. Endotoxin Res. (2005) 11:395-399.
Gares, S.L. et al., "Immunotargeting with CD154 (CD40 ligand) enhances DNA vaccine reponses in ducks," Clin. Vaccine Immun (2006) 13:958-965.
Gast, R.K. et al., "The relationship between the magnitude of the specific antibody response to experimental *Salmonella enteritidis* infection in laying hens and their production of contaminated eggs," Avian Diseases (2001) 45:425-431.
GenBank Q7YZP0, "TRP250," Nov. 28, 2006.
Grangette, C. et al., Protection against tetanus toxin after intragastric adminstration of two recombinant lactic acid bacteria: Impact and strain viability and in vivo persistence, Vaccine (2002) 20:3304-3309.
Greenspan, N.S. et al., "Defining epitopes: It's not as easy as it seems," Nature Biotechnol. (1999) 17:936-937.
Grewal, I.S. et al., "CD40 and CD154 in cell-mediated immunity," Annu. Rev. Immunology. (1998) 16:111-35.
Harcourt, J.L. et al., "CD40 ligand (CD154) improves the durability of respiratory syncytial virus DNA vaccination in BALB/c mice," Vaccine (2003) 21(21-22):2964-2979.
Hargis, B, "Live Recombinant *Salmonella* Vaccination with Novel Universal Antigen Presentation and Immune Protection," USDA Grant Project Status, Jan. 14, 2012.
Hayes, L.J. et al., "Chlamydia trachomatis major outer membrane protein epitopes expressed as fusions with LamB in an attenuated aro a strain of *Salmonella typhimurium*; their application as potential immunogens," Journal of General Microbiology (1991) 137:1557-1564.
Hoang, T.H. et al., "Recombinant Bacillus subtilis Expressing the Clostridium perfringens Alpha Toxoid Is a Candidate Orally Delivered Vaccine against Necrotic Enteritis," Infection and Immunity (2008) 76(11): 5257-5265.
Holmgren, J. et al., "Mucosal immunity. implications for vaccine development," Immunobiol. (1992) 184:157-179.
Husseiny, M.L. et al., "Rapid method for the construction of *Salmonella enterica* serovar typhimurium vaccine carrier strains," Infec. Immun. (2005) 73(3):1598-1605.
Jenkins, M.C., "Progress on developing a recombinant coccidiosis vaccine," International Journal of Parasitology (1998) 28:1111-1119.
Koch, F. et al., "High level IL-12 production by murine dendritic cells: upregulation via MHC class II and CD40 molecules and downregulation by IL-4 and IL-10," J. Exp. Med. (1996) 184:741-746.
Konjufca, V. et al., "A recombinant attenuated *Salmonella enterica* serovar Typhimurium vaccine encoding Eimeria acervulina antigen offers protection against E. acervulina challenge," Infection and Immunity (2006) 74:6785-6796.
Kotton, C.N. et al., "Enteric pathogens as vaccine vectors for foreign antigen delivery," Infect. Immun. (2004)72:5535-5547.
Kwon, Y.M. et al., "Salmonella-based vaccines for infectious diseases," Expert Review of Vaccines (2007) 6(2): 147-152.
Lapalombella, R. et al., "A Novel Raji-Burkitt's Lymphoma Model for Preclinical and Mechanistic Evaluation of CD52-Targeted Immunotherapeutic Agents," Clin. Cancer Res. (2008) 14:569-578.
Lavelle, E.C. et al., "Delivery systems and adjuvants for oral vaccines," Expert Opin. Drug Deliv. (2006) 3(6):747-762.
Layton, S.L., et al., "Vaccination of chickens with recombinant *Salmonella* expressing M2e and CD154 epitopes increases protection and decreases viral shedding after low pathogenic avian influenza challenge," Poultry Science (2009) 88(11):2244-2252.
Layton et al., Evaluation of Salmonella-vectored Campylobacter peptide epitopes for reduction of Campylobacter jejuni in broiler chickens, Clin. Vaccine Immunol. (2011) 18(3):449-454.
Lee, J.S. et al., "Surface-displayed viral antigens on salmonella carrier vaccine," Nat. Biotechnol. (2000) 18:645-648.
Li, W., "Synergistic antibody induction by antigen-CD40 ligand fusion protein as improved immunogen," Immunology (2005) 115(2):215-222.
Lowe, D.C. et al., "Characterization of candidate live oral *Salmonella typhi* vaccine strains harboring defined mutations in aroA, aroC, and htrA," Infection and Immunity Feb. 1999:700-707.
Mann, J.F. et al., "Delivery systems: a vaccine strategy for overcoming mucosal tolerance?" Expert Rev. Vaccines (2009) 8(1):103-112.

\* cited by examiner

* Indicates P < 0.001

SEQUENCE LISTING

```
<160> NUMBER OF SEQ ID NOS: 35

<210> SEQ ID NO 1
<211> LENGTH: 10
<212> TYPE: PRT
<213> ORGANISM: Eimeria maxima

<400> SEQUENCE: 1

Gly Gly Gly Phe Pro Thr Ala Ala Val Ala
```

-continued

```
1               5                    10
```

<210> SEQ ID NO 2
<211> LENGTH: 40
<212> TYPE: PRT
<213> ORGANISM: Eimeria maxima

<400> SEQUENCE: 2

```
Ala Ala Pro Glu Thr Pro Ala Val Gln Pro Lys Pro Glu Gly His
1               5                    10                   15

Glu Arg Pro Glu Pro Glu Glu Glu Lys Lys Glu Glu Gly Gly
                20                   25                   30

Gly Phe Pro Thr Ala Ala Val Ala
                35                   40
```

<210> SEQ ID NO 3
<211> LENGTH: 40
<212> TYPE: PRT
<213> ORGANISM: Eimeria maxima

<400> SEQUENCE: 3

```
Gly Gly Gly Phe Pro Thr Ala Ala Val Ala Gly Gly Val Gly Val
1               5                    10                   15

Leu Leu Ile Ala Ala Val Gly Gly Val Ala Ala Phe Thr Ser Gly
                20                   25                   30

Gly Gly Gly Ala Gly Ala Gln Glu
                35                   40
```

<210> SEQ ID NO 4
<211> LENGTH: 261
<212> TYPE: PRT
<213> ORGANISM: Homo sapiens

<400> SEQUENCE: 4

```
Met Ile Glu Thr Tyr Asn Gln Thr Ser Pro Arg Ser Ala Ala Thr Gly
1               5                    10                   15

Leu Pro Ile Ser Met Lys Ile Phe Met Tyr Leu Leu Thr Val Phe Leu
                20                   25                   30

Ile Thr Gln Met Ile Gly Ser Ala Leu Phe Ala Val Tyr Leu His Arg
                35                   40                   45

Arg Leu Asp Lys Ile Glu Asp Glu Arg Asn Leu His Glu Asp Phe Val
50                   55                   60

Phe Met Lys Thr Ile Gln Arg Cys Asn Thr Gly Glu Arg Ser Leu Ser
65                   70                   75                   80

Leu Leu Asn Cys Glu Glu Ile Lys Ser Gln Phe Glu Gly Phe Val Lys
                85                   90                   95

Asp Ile Met Leu Asn Lys Glu Glu Thr Lys Lys Glu Asn Ser Phe Glu
                100                  105                  110

Met Gln Lys Gly Asp Gln Asn Pro Gln Ile Ala Ala His Val Ile Ser
                115                  120                  125

Glu Ala Ser Ser Lys Thr Thr Ser Val Leu Gln Trp Ala Glu Lys Gly
                130                  135                  140

Tyr Tyr Thr Met Ser Asn Asn Leu Val Thr Leu Glu Asn Gly Lys Gln
145                  150                  155                  160

Leu Thr Val Lys Arg Gln Gly Leu Tyr Tyr Ile Tyr Ala Gln Val Thr
                165                  170                  175

Phe Cys Ser Asn Arg Glu Ala Ser Ser Gln Ala Pro Phe Ile Ala Ser
                180                  185                  190
```

```
Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 5
<211> LENGTH: 11
<212> TYPE: PRT
<213> ORGANISM: Homo sapiens

<400> SEQUENCE: 5

Trp Ala Glu Lys Gly Tyr Tyr Thr Met Ser Cys
1               5                   10

<210> SEQ ID NO 6
<211> LENGTH: 11
<212> TYPE: PRT
<213> ORGANISM: Gallus gallus

<400> SEQUENCE: 6

Trp Met Thr Thr Ser Tyr Ala Pro Thr Ser Ser
1               5                   10

<210> SEQ ID NO 7
<211> LENGTH: 10
<212> TYPE: PRT
<213> ORGANISM: Anas sp.

<400> SEQUENCE: 7

Trp Asn Lys Thr Ser Tyr Ala Pro Met Asn
1               5                   10

<210> SEQ ID NO 8
<211> LENGTH: 10
<212> TYPE: PRT
<213> ORGANISM: Mus sp.

<400> SEQUENCE: 8

Trp Ala Lys Lys Gly Tyr Tyr Thr Met Lys
1               5                   10

<210> SEQ ID NO 9
<211> LENGTH: 10
<212> TYPE: PRT
<213> ORGANISM: Bos taurus

<400> SEQUENCE: 9

Trp Ala Pro Lys Gly Tyr Tyr Thr Leu Ser
1               5                   10

<210> SEQ ID NO 10
<211> LENGTH: 272
<212> TYPE: PRT
<213> ORGANISM: Gallus gallus

<400> SEQUENCE: 10
```

```
Met Asn Glu Ala Tyr Ser Pro Ala Ala Pro Arg Pro Met Gly Ser Thr
1               5                   10                  15

Ser Pro Ser Thr Met Lys Met Phe Met Cys Phe Leu Ser Val Phe Met
            20                  25                  30

Val Val Gln Thr Ile Gly Thr Val Leu Phe Cys Leu Tyr Leu His Met
            35                  40                  45

Lys Met Asp Lys Met Glu Glu Val Leu Ser Leu Asn Glu Asp Tyr Ile
50                  55                  60

Phe Leu Arg Lys Val Gln Lys Cys Gln Thr Gly Glu Asp Gln Lys Ser
65                  70                  75                  80

Thr Leu Leu Asp Cys Glu Lys Val Leu Lys Gly Phe Gln Asp Leu Gln
                85                  90                  95

Cys Lys Asp Arg Thr Ala Ser Glu Glu Leu Pro Lys Phe Glu Met His
            100                 105                 110

Arg Gly His Glu His Pro His Leu Lys Ser Arg Asn Glu Thr Ser Val
            115                 120                 125

Ala Glu Glu Lys Arg Gln Pro Ile Ala Thr His Leu Ala Gly Val Lys
            130                 135                 140

Ser Asn Thr Thr Val Arg Val Leu Lys Trp Met Thr Thr Ser Tyr Ala
145                 150                 155                 160

Pro Thr Ser Ser Leu Ile Ser Tyr His Glu Gly Lys Leu Lys Val Glu
                165                 170                 175

Lys Ala Gly Leu Tyr Tyr Ile Tyr Ser Gln Val Ser Phe Cys Thr Lys
            180                 185                 190

Ala Ala Ala Ser Ala Pro Phe Thr Leu Tyr Ile Tyr Leu Tyr Leu Pro
            195                 200                 205

Met Glu Glu Asp Arg Leu Leu Met Lys Gly Leu Asp Thr His Ser Thr
210                 215                 220

Ser Thr Ala Leu Cys Glu Leu Gln Ser Ile Arg Glu Gly Gly Val Phe
225             230                 235                 240

Glu Leu Arg Gln Gly Asp Met Val Phe Val Asn Val Thr Asp Ser Thr
                245                 250                 255

Ala Val Asn Val Asn Pro Gly Asn Thr Tyr Phe Gly Met Phe Lys Leu
            260                 265                 270
```

<210> SEQ ID NO 11
<211> LENGTH: 70
<212> TYPE: PRT
<213> ORGANISM: Eimeria maxima

<400> SEQUENCE: 11

```
Ala Ala Pro Glu Thr Pro Ala Val Gln Pro Lys Pro Glu Glu Gly His
1               5                   10                  15

Glu Arg Pro Glu Pro Glu Glu Glu Lys Lys Glu Glu Glu Glu Gly Gly
            20                  25                  30

Gly Phe Pro Thr Ala Ala Val Ala Gly Gly Val Gly Gly Val Leu Leu
            35                  40                  45

Ile Ala Ala Val Gly Gly Val Ala Ala Phe Thr Ser Gly Gly Gly
        50                  55                  60

Gly Ala Gly Ala Gln Glu
65                  70
```

<210> SEQ ID NO 12
<211> LENGTH: 30
<212> TYPE: DNA
<213> ORGANISM: Eimeria maxima

```
<400> SEQUENCE: 12
ggtggtggtt ttccgaccgc ggcggttgcg                                              30

<210> SEQ ID NO 13
<211> LENGTH: 120
<212> TYPE: DNA
<213> ORGANISM: Eimeria maxima

<400> SEQUENCE: 13
gcggcgccgg aaaccccggc ggttcagccg aaagccgaag aaggtcatga acgtccggaa             60
ccggaagaag aagaagaaaa aaaagaagaa ggtggtggtt ttccgaccgc ggcggttgcg            120

<210> SEQ ID NO 14
<211> LENGTH: 120
<212> TYPE: DNA
<213> ORGANISM: Eimeria maxima

<400> SEQUENCE: 14
ggtggtggtt ttccgaccgc ggcggttgcg ggtggtgttg gtggtgttct gctgatcgcg             60
gcggttggtg gtggtgttgc ggcgtttacc tccggtggtg gtggtgcggg tgcgcaggaa            120

<210> SEQ ID NO 15
<211> LENGTH: 210
<212> TYPE: DNA
<213> ORGANISM: Eimeria maxima

<400> SEQUENCE: 15
gcggcgccgg aaaccccggc ggttcagccg aaagccgaag aaggtcatga acgtccggaa             60
ccggaagaag aagaagaaaa aaaagaagaa ggtggtggtt ttccgaccgc ggcggttgcg            120
ggtggtgttg gtggtgttct gctgatcgcg gcggttggtg gtggtgttgc ggcgtttacc            180
tccggtggtg gtggtgcggg tgcgcaggaa                                             210

<210> SEQ ID NO 16
<211> LENGTH: 18
<212> TYPE: DNA
<213> ORGANISM: Artificial Sequence
<220> FEATURE:
<223> OTHER INFORMATION: I-SceI enzyme recognition sequence

<400> SEQUENCE: 16
tagggataac agggtaat                                                           18

<210> SEQ ID NO 17
<211> LENGTH: 20
<212> TYPE: DNA
<213> ORGANISM: Artificial Sequence
<220> FEATURE:
<223> OTHER INFORMATION: loop 9 up

<400> SEQUENCE: 17
tgtacaagtg gacgccaatc                                                         20

<210> SEQ ID NO 18
<211> LENGTH: 24
<212> TYPE: DNA
<213> ORGANISM: Artificial Sequence
<220> FEATURE:
<223> OTHER INFORMATION: loop 9 up

<400> SEQUENCE: 18
```

```
gttatcgccg tctttgatat agcc                                              24

<210> SEQ ID NO 19
<211> LENGTH: 20
<212> TYPE: DNA
<213> ORGANISM: Artificial Sequence
<220> FEATURE:
<223> OTHER INFORMATION: loop 9 dn

<400> SEQUENCE: 19
atttcccgtt atgccgcagc                                                   20

<210> SEQ ID NO 20
<211> LENGTH: 20
<212> TYPE: DNA
<213> ORGANISM: Artificial Sequence
<220> FEATURE:
<223> OTHER INFORMATION: loop 9 dn

<400> SEQUENCE: 20
gttaaacaga gggcgacgag                                                   20

<210> SEQ ID NO 21
<211> LENGTH: 68
<212> TYPE: DNA
<213> ORGANISM: Artificial Sequence
<220> FEATURE:
<223> OTHER INFORMATION: I-SceI/Kmr gene

<400> SEQUENCE: 21
gctatatcaa agacggcgat aactaactat aacggtccta aggtagcgaa tttccgggga       60
tccgtcga                                                                68

<210> SEQ ID NO 22
<211> LENGTH: 40
<212> TYPE: DNA
<213> ORGANISM: Artificial Sequence
<220> FEATURE:
<223> OTHER INFORMATION: I-SceI/Kmr gene

<400> SEQUENCE: 22
gctgcggcat aacgggaaat tgtaggctgg agctgcttcg                             40

<210> SEQ ID NO 23
<211> LENGTH: 20
<212> TYPE: DNA
<213> ORGANISM: Artificial Sequence
<220> FEATURE:
<223> OTHER INFORMATION: inside Kmr gene: sequencing

<400> SEQUENCE: 23
caaaagcgct ctgaagttcc                                                   20

<210> SEQ ID NO 24
<211> LENGTH: 20
<212> TYPE: DNA
<213> ORGANISM: Artificial Sequence
<220> FEATURE:
<223> OTHER INFORMATION: inside Kmr gene: sequencing

<400> SEQUENCE: 24
gcgtgagggg atcttgaagt                                                   20

<210> SEQ ID NO 25
<211> LENGTH: 69
```

```
<212> TYPE: DNA
<213> ORGANISM: Artificial Sequence
<220> FEATURE:
<223> OTHER INFORMATION: SEQ1 hCD154/ loop 9 up

<400> SEQUENCE: 25
ggaggacgca accgccgcgg tcggaaaacc accaccggag gaggagttat cgccgtcttt    60
gatatagcc                                                           69

<210> SEQ ID NO 26
<211> LENGTH: 82
<212> TYPE: DNA
<213> ORGANISM: Artificial Sequence
<220> FEATURE:
<223> OTHER INFORMATION: SEQ1hCD154/ loop 9 down

<400> SEQUENCE: 26
ccgcggcggt tgcgtcctcc tcctgggcag aaaaaggtta ttataccatg tcttcctcct    60
ccatttcccg ttatgccgca gc                                            82

<210> SEQ ID NO 27
<211> LENGTH: 113
<212> TYPE: DNA
<213> ORGANISM: Artificial Sequence
<220> FEATURE:
<223> OTHER INFORMATION: SEQ2-hCD154/ loop 9 up

<400> SEQUENCE: 27
ttttcttctt cttcttccgg ttccggacgt tcatgacctt cttcggcttt cggctgaacc    60
gccggggttt ccggcgccgc ggaggaggag ttatcgccgt ctttgatata gcc          113

<210> SEQ ID NO 28
<211> LENGTH: 129
<212> TYPE: DNA
<213> ORGANISM: Artificial Sequence
<220> FEATURE:
<223> OTHER INFORMATION: SEQ2-hCD154/ loop 9 down

<400> SEQUENCE: 28
accggaagaa gaagaagaaa aaaagaaga aggtggtggt tttccgaccg cggcggttgc    60
gtcctcctcc tgggcagaaa aaggttatta taccatgtct tcctcctcca tttcccgtta   120
tgccgcagc                                                          129

<210> SEQ ID NO 29
<211> LENGTH: 113
<212> TYPE: DNA
<213> ORGANISM: Artificial Sequence
<220> FEATURE:
<223> OTHER INFORMATION: SEQ3 hCD154/ loop 9 up

<400> SEQUENCE: 29
gcaacaccac caccaaccgc cgcgatcagc agaacaccac caacaccacc cgcaaccgcc    60
gcggtcggaa aaccaccacc ggaggaggag ttatcgccgt ctttgatata gcc          113

<210> SEQ ID NO 30
<211> LENGTH: 129
<212> TYPE: DNA
<213> ORGANISM: Artificial Sequence
<220> FEATURE:
<223> OTHER INFORMATION: SEQ3-hCD154/ loop 9 down

<400> SEQUENCE: 30
```

```
ggcggttggt ggtggtgttg cggcgtttac ctccggtggt ggtggtgcgg gtgcgcagga    60
atcctcctcc tgggcagaaa aaggttatta taccatgtct tcctcctcca tttcccgtta   120
tgccgcagc                                                          129
```

```
<210> SEQ ID NO 31
<211> LENGTH: 20
<212> TYPE: DNA
<213> ORGANISM: Artificial Sequence
<220> FEATURE:
<223> OTHER INFORMATION: outer regions of loop 9: sequencing

<400> SEQUENCE: 31
gccatctcgc ttggtgataa                                               20
```

```
<210> SEQ ID NO 32
<211> LENGTH: 20
<212> TYPE: DNA
<213> ORGANISM: Artificial Sequence
<220> FEATURE:
<223> OTHER INFORMATION: outer regions of loop 9: sequencing

<400> SEQUENCE: 32
cgctggtatt ttgcggtaca                                               20
```

```
<210> SEQ ID NO 33
<211> LENGTH: 87
<212> TYPE: DNA
<213> ORGANISM: Artificial Sequence
<220> FEATURE:
<223> OTHER INFORMATION: TRAP-CD154

<400> SEQUENCE: 33
tcctcctccg gtggtggttt ccgaccgcg gcggttgcgt cctcctcctg ggcagaaaaa    60
ggttattata ccatgtcttc ctcctcc                                       87
```

```
<210> SEQ ID NO 34
<211> LENGTH: 177
<212> TYPE: DNA
<213> ORGANISM: Artificial Sequence
<220> FEATURE:
<223> OTHER INFORMATION: TRAP-US-CD154

<400> SEQUENCE: 34
tcctcctccg cggcgccgga aaccccggcg gttcagccga aagccgaaga aggtcatgaa    60
cgtccggaac cggaagaaga agaagaaaaa aaagaagaag gtggtggttt ccgaccgcg   120 gcggttgcgt cctcctcctg ggcagaaaaa ggttattata ccatgtcttc ctcctcc     177
```

```
<210> SEQ ID NO 35
<211> LENGTH: 177
<212> TYPE: DNA
<213> ORGANISM: Artificial Sequence
<220> FEATURE:
<223> OTHER INFORMATION: TRAP-DS-CD154

<400> SEQUENCE: 35
tcctcctccg gtggtggttt ccgaccgcg gcggttgcgg gtggtgttgg tggtgttctg    60
ctgatcgcgg cggttggtgg tggtgttgcg gcgtttacct ccggtggtgg tggtgcgggt   120
gcgcaggaat cctcctcctg ggcagaaaaa ggttattata ccatgtcttc ctcctcc     177
```

US 10,842,858 B2

COMPOSITIONS AND METHODS OF ENHANCING IMMUNE RESPONSES TO EIMERIA

CROSS-REFERENCE TO RELATED APPLICATIONS

This application is a Continuation of U.S. patent application Ser. No. 14/623,050, filed Feb. 16, 2015 and issuing as U.S. Pat. No. 10,016,493 on Jul. 10, 2018, which is a Continuation of U.S. patent application Ser. No. 12/740,608, filed Dec. 28, 2010 and issuing as U.S. Pat. No. 8,956,849 on Feb. 17, 2015, which application is a national stage filing under 35 U.S.C. 371 of International Application No. PCT/US2008/082254, filed Nov. 3, 2008, which claims the benefit of priority of U.S. Provisional Application Ser. No. 60/984,612, filed Nov. 1, 2007, all of which are incorporated herein by reference in their entirety.

STATEMENT REGARDING FEDERALLY SPONSORED RESEARCH

None.

SEQUENCE LISTING

A Sequence Listing accompanies this application and is incorporated herein by reference in its entirety. The Sequence Listing was filed with the application.

INTRODUCTION

Coccidiosis, an infectious disease of poultry, swine, and cattle caused by the Apicomplexan protozoal parasite *Eimeria*, presents problems worldwide. Coccidiosis is among the top ten infectious diseases of poultry in terms of its economic impact on the poultry industry. Other members of the Apicomplexan family also cause disease, including *Plasmodium, Cryptosporidium* and *Toxoplasma* which are the causative agents of malaria, cryptosporidiosis and toxoplasmosis, respectively. The vaccines currently available against *Eimeria* are based on controlled low dosage of essentially fully virulent but drug-sensitive *Eimeria* parasites. Vaccination with current *Eimeria*-based vaccines produces substantial vaccine-reaction morbidity and economic losses in vaccinated flocks. Thus an effective low-virulence vaccine against *Eimeria* is needed. An effective vaccine for *Eimeria* may also prove useful as a vaccine against other Apicomplexan parasites.

SUMMARY

A vaccine comprising a first polynucleotide sequence encoding a TRAP polypeptide or an immunogenic fragment thereof is disclosed. The TRAP polypeptide may comprise comprises SEQ ID NO:1, SEQ ID NO:2, or SEQ ID NO:3, or an immunogenic fragment thereof. The vaccines optionally further include a second polynucleotide sequence encoding a CD154 polypeptide capable of binding CD40. The CD154 polypeptides include fewer than 50 amino acids and comprise amino acids 140-149, or a homolog thereof.

Vaccines according to the present invention may be comprised within a vector, such as a virus, bacterium, or liposome. In one aspect, a vaccine comprising a *Salmonella enteritidis* comprising a first polynucleotide sequence encoding a TRAP polypeptide is provided.

In still another aspect, the invention includes methods of enhancing the immune response against an Apicomplexan parasite in a subject by administering a vaccine according to the present invention.

In a still further aspect, the invention includes methods of reducing morbidity associated with infection with an Apicomplexan parasite in a subject by administering a vaccine according to the present invention.

BRIEF DESCRIPTION OF THE DRAWINGS

FIG. 2A shows the construction of the PCR-A construct using the overlapping PCR techniques described in the Examples. FIG. 2B shows the construction of the PCR-B construct as described in the Examples.

DETAILED DESCRIPTION

Figure 1:
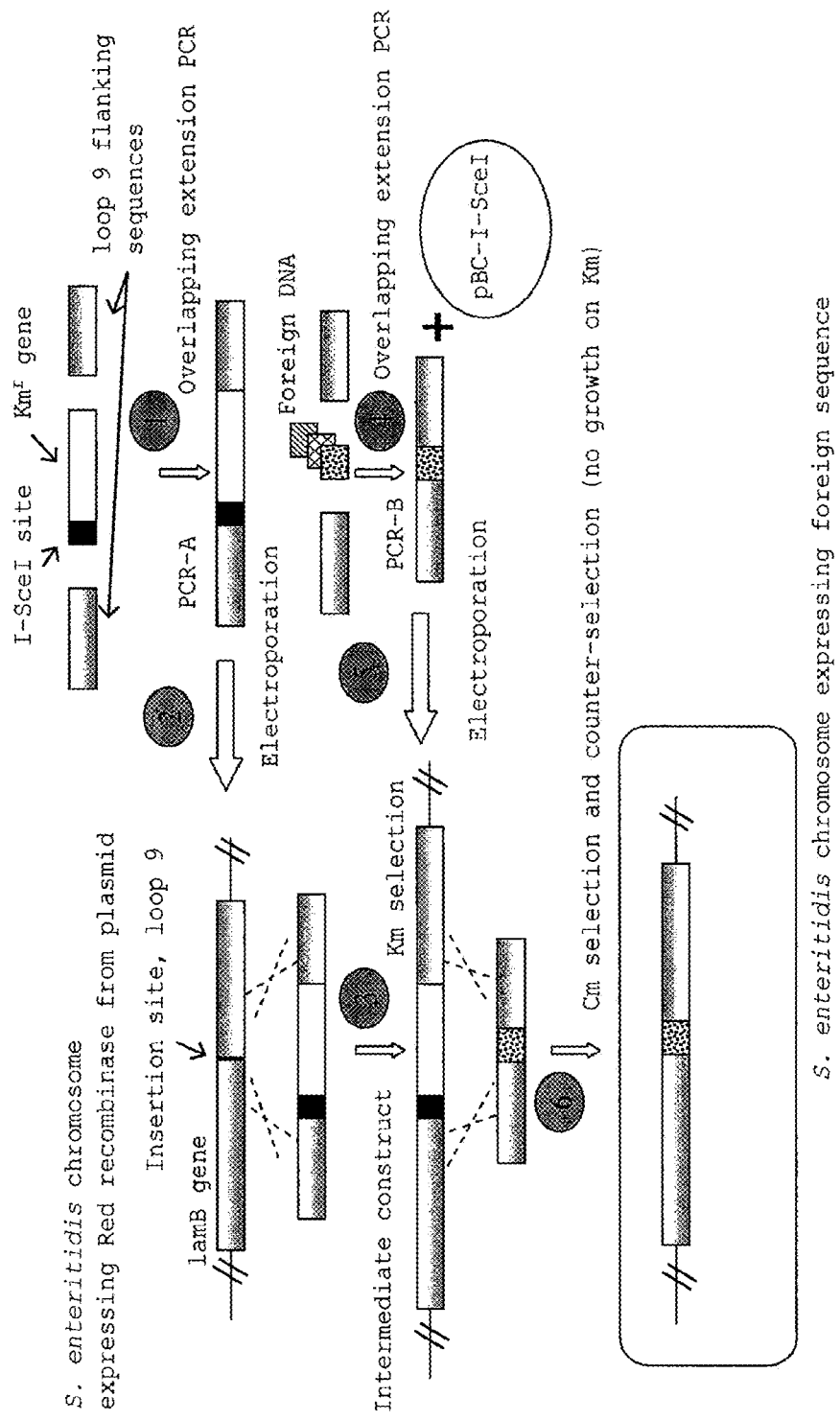
FIG. 1 depicts the scheme for making site-directed mutations in *Salmonella enteritidis*.

Recombinant DNA technologies enable relatively easy manipulation of many bacterial and viral species. Some bacteria and viruses are mildly pathogenic or non-pathogenic, but are capable of generating a robust immune response. These bacteria and viruses make attractive vaccines for eliciting an immune response to antigens. Bacterial or viral vaccines may mimic a natural infection and produce robust and long lasting mucosal immunity. Vaccines are often relatively inexpensive to produce and administer. In addition, such vectors can often carry more than one antigen and may provide protection against multiple infectious agents.

In one aspect, a vaccine comprising a first polynucleotide sequence encoding a TRAP polypeptide or an immunogenic fragment thereof is provided. The TRAP polypeptide may comprise SEQ ID NO:11 or an immunogenic fragment of SEQ ID NO:11. A vaccine includes any composition comprising a polynucleotide encoding an antigenic polypeptide that is capable of eliciting an immune response to the polypeptide. In another aspect, the use of vectors, such as bacterial vectors, for vaccination and generation of immune responses against *Eimeria* or other Apicomplexan parasites such as *Plasmodium* (the causative agent of malaria), *Toxoplasma* and *Cryptosporidium* is disclosed. *Salmonella* strains make suitable vectors because bacterial genes may be mutated or attenuated to create bacteria with low to no pathogenesis to the infected or immunized subject, while maintaining immunogenicity.

A high molecular mass, asexual stage antigen from *Eimeria* maxima (EmTFP250) was demonstrated to be a target for maternal antibodies produced by breeding hens infected with this protozoan parasite. Analysis of the amino acid sequence of the antigen revealed a novel member of the TRAP (thrombospondin-related anonymous protein) family, containing 16 thrombospondin type-1 repeats and 31 epidermal growth factor-like calcium binding domains. EmTFP250 or TRAP also contains two low complex, hydrophilic regions rich in glutamic acid and glycine residues, and a transmembrane domain/cytosolic tail associated with parasite gliding motility that is highly conserved within apicomplexan microneme proteins. Several potential epitopes were selected and are identified in SEQ ID NO:1-3 and 11. Due to the conserved nature of this antigen, expression of these epitopes by a vector may induce protective immunity against multiple Apicomplexan parasites.

*Salmonella* may provide a useful vector because it can survive the gastrointestinal tract of the host and give rise to a mucosal immune response. Oral vaccines using a *Salmonella* vector produce a robust mucosal immune response and are relatively easy to administer to both animals and humans. However, many of the current *Salmonella* vaccine strains are not as effective in generating a strong protective immune response as compared to their more virulent counterparts. Virulent strains provide a robust immune response but may also cause significant morbidity to the vaccinated subject. A *Salmonella* strain that could be used for effective mucosal, e.g., oral, vaccination would provide a vector that could be used to readily vaccinate a subject against one or more pathogenic agents, such as Apicomplexan parasites.

A *Salmonella enteritidis* strain useful as a vector, and various recombinant vectors made using this strain, are described. Specifically, a *Salmonella enteritidis* 13A (SE13A) capable of expressing an exogenous TRAP polypeptide is provided. In addition, a vaccine and methods of enhancing an immune response in a subject by administering the vaccine comprising a TRAP polynucleotide sequence encoding a TRAP polypeptide and a CD154 polynucleotide sequence encoding a polypeptide of CD154 or a homolog thereof that is capable of binding to CD40 are disclosed. The vaccines may be used to enhance an immune response against *Eimeria* or another Apicomplexan parasite, such as *Plasmodium, Toxoplasma* or *Cryptosporidium*, or may be used to reduce the morbidity associated with an infection caused by an Apicomplexan parasite.

A wild-type isolate of *Salmonella, Salmonella enteritidis* 13A (SE13A) (deposited with the American Type Culture Collection (ATCC) on Sep. 13, 2006, deposit number PTA-7871), was selected based upon its unusual ability to cause mucosal colonization and sub-mucosal translocation in chickens, permitting robust presentation of associated antigens or epitopes in commercial chickens. Importantly, this wild-type *Salmonella* isolate causes no clinically detectable disease or loss of performance in commercial chickens, indicating little disease-causing potential of the wild-type *Salmonella* in vertebrate animals.

The SE13A isolate may be further attenuated by inactivating at least one gene necessary for sustained replication of the bacteria outside of laboratory or manufacturing conditions. Attenuated or variant *Salmonella* strains that can be used as vectors are described below. SE13A was used to generate attenuated *Salmonella* strains to develop vaccines and generate enhanced immune responses. SE13A is invasive, non-pathogenic for poultry and causes no measurable morbidity. These features result in an enhanced immune response as compared to non-invasive bacterial vectors. Attenuation of SE13A by mutation of genes that limit the ability of the bacterium to spread may increase the safety of the vaccine. SE13A strains with mutations in aroA or htrA retain the ability to generate an immune response, but have limited replication in the host. Thus, the attenuation increases the safety of the vector without compromising the immunogenicity.

Mutations may be made in a variety of other *Salmonella* genes including, but not limited to, cya, crp, asd, cdt, phoP, phoQ, ompR, outer membrane proteins, dam, htrA or other stress related genes, aro, pur and gua. As shown in the Examples, mutations in aroA and htrA were found to attenuate SE13A. The aro genes are enzymes involved in the shikimate biosynthesis pathway or the aromatase pathway and aro mutants are auxotrophic for the aromatic amino acids tryptophan, tyrosine and phenylalanine. htrA is a stress response gene that encodes a periplasmic protease that degrades aberrant proteins. Mutants in htrA are also attenuated and display increased sensitivity to hydrogen peroxide.

The mutations in aroA and htrA described in the Examples are deletion mutations, but the mutations can be made in a variety of ways. Suitably, the mutations are non-reverting mutations that cannot be repaired in a single step. Suitable mutations include deletions, inversions, insertions and substitutions. A vector may include more than one mutation, for example a vector may contain mutations in both aroA and htrA. Methods of making such mutations are well known in the art.

Polynucleotides encoding TRAP polypeptide antigens and other antigens from any number of pathogenic organisms may be inserted into the vector (e.g., SE13A) and expressed by the bacteria. The expression of these polynucleotides by the vector will allow generation of antigenic polypeptides following immunization of the subject. The polynucleotides may be inserted into the chromosome of the bacteria or encoded on plasmids or other extrachromosomal DNA. Those of skill in the art will appreciate that numerous methodologies exist for obtaining expression of polynucleotides in vectors such as *Salmonella*. The polynucleotides may be operably connected to a promoter (e.g., a constitutive promoter, an inducible promoter, etc.) by methods known to those of skill in the art. Suitably, polynucleotides encoding TRAP antigens are inserted into a bacterial polynucleotide that is expressed. Suitably, the bacterial polynucleotide encodes a transmembrane protein, and the polynucleotide encoding the TRAP antigen is inserted into the bacterial polynucleotide sequence to allow expression of the TRAP antigen on the surface of the bacteria. For example, the polynucleotide encoding TRAP may be inserted in frame into the bacterial polynucleotide in a region encoding an external loop region of a transmembrane protein such that the bacterial polynucleotide sequence remains in frame. See Example 1.

Alternatively, the first polynucleotide encoding TRAP antigen may be inserted into a polynucleotide encoding a secreted polypeptide. Those of skill in the art will appreciate that the polynucleotide encoding the TRAP antigen could be inserted in a wide variety of bacterial polynucleotides to provide expression and presentation of the TRAP antigen to the immune cells of a subject treated with the vaccine. In the Examples, a first polynucleotide encoding the TRAP polypeptide was inserted into loop 9 of the lamB gene of SE13A. The polynucleotide encoding the TRAP antigen may be included in a single copy or more than one copy. A bacterial vector containing multiple copies of the TRAP antigen inserted into loop 9 of lamB may also be generated. Alternatively, multiple copies of an epitope may be inserted into the bacterial vector at more than one location.

Suitably the first polynucleotide encodes a portion of the TRAP polypeptide or the entire TRAP polypeptide. The polynucleotide may be inserted into the vector. In the Examples, three polypeptides (SEQ ID NO:1-3) were incorporated into SE13A. Suitably, the portion of the TRAP polypeptide inserted into the vector is an immunogenic fragment. An immunogenic fragment is a peptide or polypeptide capable of eliciting a cellular or humoral immune response. Suitably, an immunogenic fragment of TRAP may be 6 or more consecutive amino acids, 10 or more amino acids, 15 or more amino acids or 20 or more amino acids of the full-length protein sequence.

Other suitable epitopes for inclusion in a vaccine having TRAP comprised within a vector include, but are not limited to, polynucleotides encoding other *Eimeria*-related polypeptides. One of skill in the art will appreciate that a variety of sequences may be used in combination with any other antigen and may also be used in conjunction with polypeptides encoding immune stimulatory peptides such as a polypeptide of CD154.

As described in more detail below, a vaccine including a vector may include a CD154 polypeptide that is capable of binding CD40 in the subject and stimulating the subject to respond to the vector and its associated antigen. Involvement of dendritic cells (DCs) is essential for the initiation of a powerful immune response as they possess the unique ability to activate naïve T cells, causing T cell expansion and differentiation into effector cells. It is the role of the DC, which is an antigen presenting cell (APC) found in virtually all tissues of the body, to capture antigens, transport them to associated lymphoid tissue, and then present them to naïve T cells. Upon activation by DCs, T cells expand, differentiate into effector cells, leave the secondary immune organs, and enter peripheral tissues. Activated cytotoxic T cells (CTLs) are able to destroy virus-infected cells, tumor cells or even APCs infected with intracellular parasites (e.g., *Salmonella*) and have been shown to be critical in the protection against viral infection. CD40 is a member of the TNF-receptor family of molecules and is expressed on a variety of cell types, including professional antigen-presenting cells (APCs), such as DCs and B cells. Interaction of CD40 with its ligand CD154 is extremely important and stimulatory for both humoral and cellular immunity. Stimulation of DCs via CD40, expressed on the surface of DCs, can be simulated by anti-CD40 antibodies. In the body, however, this occurs by interaction with the natural ligand for CD40 (i.e. CD154) expressed on the surface of activated T-cells. Interestingly, the CD40-binding regions of CD154 have been identified. The CD40-binding region of CD154 may be expressed on the surface of a vector, such as a *Salmonella* vector, and results in an enhanced immune response against a co-presented peptide sequence.

As described above, polynucleotides encoding CD154 polypeptides may be inserted into the chromosome of the vector or maintained extrachromosomally. A CD154 polypeptide may be a portion of CD154 full-length protein or the entire CD154 protein. Suitably, the CD154 polypeptide is capable of binding CD40. One of skill in the art will appreciate that these polynucleotides can be inserted in frame in a variety of polynucleotides and expressed in different parts of the vector or may be secreted. The polynucleotide encoding a CD154 polypeptide capable of enhancing the immune response to TRAP may also encode the TRAP antigen. The polynucleotide encoding a CD154 polypeptide may be linked to the polynucleotide encoding the TRAP antigen, such that in the vector, the CD154 polypeptide and the TRAP antigen are present on the same polypeptide. In the Examples, a polynucleotide encoding a polypeptide of CD154 that is capable of binding to CD40 also encodes the TRAP antigen. See SEQ ID NOS: 1, 2, 3 and 11 in the attached sequence listing. In the Examples, the polynucleotides (SEQ ID NO:13-15) encoding the TRAP antigen and the polynucleotide encoding the CD154 polypeptide are both inserted in loop 9 of the lamB gene. Those of skill in the art will appreciate that bacterial polynucleotides encoding other transmembrane proteins and other loops of the lamB gene may also be used.

As discussed above, a CD154 polynucleotide encoding a CD154 polypeptide that is capable of enhancing the immune response to the antigen may be included in the vaccine. Suitably, the CD154 polypeptide is fewer than 50 amino acids long, more suitably fewer than 40, fewer than 30 or fewer than 20 amino acids in length. The polypeptide may be between 10 and 15 amino acids, between 10 and 20 amino acids or between 10 and 25 amino acids in length. The CD154 sequence and CD40 binding region are not highly conserved among the various species. The CD154 sequences of chicken and human are provided in SEQ ID NO:10 and SEQ ID NO:4, respectively.

The CD40 binding regions of CD154 have been determined for a number of species, including human, chicken, duck, mouse and cattle and are shown in SEQ ID NO:5, SEQ ID NO:6, SEQ ID NO:7, SEQ ID NO:8, and SEQ ID NO:9, respectively. Although there is variability in the sequences in the CD40 binding region between species, the human CD154 polypeptide was able to enhance the immune response in chickens. Therefore, one may practice the invention using species specific CD154 polypeptides or a heterologous CD 154 polypeptide.

In the Examples, several SE13A recombinant bacteria were generated. In each of the SE13A strains containing both the TRAP and CD154 polynucleotides, the TRAP polypepetide and the CD154 polypeptide were encoded on the same polynucleotide and were in frame with each other and with the *Salmonella* lamB polynucleotide in which they were inserted. In alternative embodiments, the CD154 polypeptide and the TRAP polypeptide may be encoded by distinct polynucleotides. SE13A aroA htrA TRAP contains a deletion in aroA and htrA and encodes both the TRAP epitope (SEQ ID NO:1-3) and optionally the CD154 polypeptide (SEQ ID NO:4) inserted into loop 9 of lamB.

Compositions comprising an attenuated *Salmonella* strain and a pharmaceutically acceptable carrier are also provided. A pharmaceutically acceptable carrier is any carrier suitable for in vivo administration. Examples of pharmaceutically acceptable carriers suitable for use in the composition include, but are not limited to, water, buffered solutions, glucose solutions or bacterial culture fluids. Additional components of the compositions may suitably include, for example, excipients such as stabilizers, preservatives, diluents, emulsifiers and lubricants. Examples of pharmaceutically acceptable carriers or diluents include stabilizers such as carbohydrates (e.g., sorbitol, mannitol, starch, sucrose, glucose, dextran), proteins such as albumin or casein, protein-containing agents such as bovine serum or skimmed milk and buffers (e.g., phosphate buffer). Especially when such stabilizers are added to the compositions, the composition is suitable for freeze-drying or spray-drying.

Methods of enhancing immune responses in a subject by administering a vaccine containing a TRAP polypeptide and a CD154 polypeptide capable of binding to CD40 and activating CD40 are also provided. The vaccine comprising the polynucleotide encoding a CD154 polypeptide capable of binding to CD40 is administered to a subject in an amount effective to enhance the immune response of the subject to the vaccine. Suitably, the vaccine contains a polynucleotide encoding a polypeptide including amino acids 140-149 of the human CD154 polypeptide (SEQ ID NO:4) or a homolog thereof. Therefore, a homologue of amino acid 140-149 derived from one species may be used to stimulate an immune response in a distinct species.

Several suitable polypeptides are identified herein. Suitably, the polynucleotide encodes a CD154 polypeptide from the same species as the subject. Suitably, a polynucleotide encoding the polypeptide of SEQ ID NO:5 is used in human subjects, a polynucleotide encoding the polypeptide of SEQ ID NO:6 is used in chickens, a polynucleotide encoding the polypeptide of SEQ ID NO:7 is used in ducks, a polynucleotide encoding the polypeptide of SEQ ID NO:8 is used in mice, and a polynucleotide encoding the polypeptide of SEQ ID NO:9 is used in cows. In the Examples, the human CD154 polypeptide (SEQ ID NO:5) was used in a chicken vaccine and was demonstrated to enhance the immune response to a foreign antigen. Thus other heterologous combinations of CD154 polypeptides and subjects may be useful in the methods of the invention. The CD154 polypeptide may be used to enhance the immune response in the subject to any foreign antigen or antigenic polypeptide present in the vaccine in addition to the TRAP polypeptide. One of skill in the art will appreciate that the CD154 polypeptide could be used to enhance the immune response to more than one antigenic polypeptide present in a vaccine.

The polypeptide from CD154 stimulates an immune response at least in part by binding to its receptor, CD40. The Examples used a polypeptide homologous to the CD154 polypeptide which is expressed on immune cells of the subject and which is capable of binding to the CD40 receptor on macrophages and other antigen presenting cells. Binding of this ligand-receptor complex stimulates macrophage (and macrophage lineage cells such as dendritic cells) to enhance phagocytosis and antigen presentation while increasing cytokine secretions known to activate other local immune cells (such as B-lymphocytes). As such, molecules associated with the CD154 peptide are preferentially targeted for immune response and expanded antibody production.

Potential vectors for use in the methods include, but are not limited to, *Salmonella*(*Salmonella enteritidis*), *Shigella*, *Escherichia* (*E. coli*), *Yersinia*, *Bordetella*, *Lactococcus*, *Lactobacillus*, *Bacillus*, *Streptococcus*, *Vibrio* (*Vibrio cholerae*), *Listeria*, adenovirus, poxvirus, herpesvirus, alphavirus, and adeno-associated virus.

In addition, methods of enhancing an immune response against an Apicomplexan parasite and methods of reducing morbidity associated with subsequent infection with an Apicomplexan parasite are disclosed. Briefly, the methods comprise administering to a subject a vaccine comprising a first polynucleotide sequence encoding a TRAP polypeptide in an effective amount. The TRAP polypeptides may include SEQ ID NO:1-3 and 11. The insertion of the TRAP polypeptides into the vector may be accomplished in a variety of ways known to those of skill in the art, including but not limited to the scarless site-directed mutation system described in BMC Biotechnol. 2007 Sep. 17: 7(1): 59, Scarless and Site-directed Mutagenesis in *Salmonella enteritidis* chromosome, which is incorporated herein by reference in its entirety. The vector may also be engineered to express the TRAP polypeptides in conjunction with other polypeptides capable of enhancing the immune response as discussed above, such as in SEQ ID NO:4 and SEQ ID NO:10. In particular, a polypeptide of CD154 capable of binding CD40 may be expressed by the vector to enhance the immune response of the subject to the TRAP polypeptide. Optionally, the vector is a bacterium, such as *Salmonella* enteritidis.

The useful dosage of the vaccine to be administered will vary depending on the age, weight and species of the subject, the mode and route of administration and the type of pathogen against which an immune response is sought. The composition may be administered in any dose sufficient to evoke an immune response. For bacterial vaccines, it is envisioned that doses ranging from $10^3$ to $10^{10}$ bacteria, from $10^4$ to $10^9$ bacteria, or from $10^5$ to $10^7$ bacteria are suitable. The composition may be administered only once or may be administered two or more times to increase the immune response. For example, the composition may be administered two or more times separated by one week, two weeks, or by three or more weeks. The bacteria are suitably viable prior to administration, but in some embodiments the bacteria may be killed prior to administration. In some embodiments, the bacteria may be able to replicate in the subject, while in other embodiments the bacteria may not be capable of replicating in the subject.

For administration to animals or humans, the compositions may be administered by a variety of means including, but not limited to, intranasally, mucosally, by spraying, intradermally, parenterally, subcutaneously, orally, by aerosol or intramuscularly. Eye-drop administration or addition to drinking water or food are additionally suitable. For chickens, the compositions may be administered in ovo.

Some embodiments of the invention provide methods of enhancing immune responses in a subject. Suitable subjects may include, but are not limited to, vertebrates, suitably mammals, suitably a human, and birds, suitably poultry such as chickens. Other animal models of infection may also be used Enhancing an immune response includes, but is not limited to, inducing a therapeutic or prophylactic effect that is mediated by the immune system of the subject. Specifically, enhancing an immune response may include, but is not limited to, enhanced production of antibodies, enhanced class switching of antibody heavy chains, maturation of antigen presenting cells, stimulation of helper T cells, stimulation of cytolytic T cells or induction of T and B cell memory.

It is envisioned that several epitopes or antigens from the same or different pathogens may be administered in combination in a single vaccine to generate an enhanced immune response against multiple antigens. Recombinant vaccines may encode antigens from multiple pathogenic microorganisms, viruses or tumor associated antigens. Administration of vaccine capable of expressing multiple antigens has the advantage of inducing immunity against two or more diseases at the same time. For example, live attenuated bacteria, such as *Salmonella enteritidis* 13A, provide a suitable vector for eliciting an immune response against multiple antigens.

Bacterial vaccines may be constructed using exogenous polynucleotides encoding antigens which may be inserted into the bacterial genome at any non-essential site or alternatively may be carried on a plasmid using methods well known in the art. One suitable site for insertion of polynucleotides is within external portions of transmembrane proteins or coupled to sequences that target the exogenous polynucleotide for secretory pathways. One example of a suitable transmembrane protein for insertion of polynucleotides is the lamB gene. In the Examples, TRAP and CD154 polynucleotides were inserted into loop 9 of the lamB sequence.

Exogenous polynucleotides include, but are not limited to, polynucleotides encoding antigens selected from pathogenic microorganisms or viruses and include polynucleotides that are expressed in such a way that an effective immune response is generated. Such polynucleotides may be derived from pathogenic viruses such as influenza (e.g., M2e, hemagglutinin, or neuraminidase), herpesviruses (e.g., the genes encoding the structural proteins of herpesviruses), retroviruses (e.g., the gp160 envelope protein), adenoviruses, paramyxoviruses, coronaviruses and the like. Exogenous polynucleotides can also be obtained from pathogenic bacteria, e.g., genes encoding bacterial proteins such as toxins, and outer membrane proteins. Further, exogenous polynucleotides from parasites, such as other Apicomplexan parasites are attractive candidates for use of a vector vaccine.

Polynucleotides encoding polypeptides involved in triggering the immune system may also be included in a vector, such as a live attenuated *Salmonella* vaccine. The polynucleotides may encode immune system molecules known for their stimulatory effects, such as an interleukin, Tumor Necrosis Factor, an interferon, or another polynucleotide involved in immune-regulation. The vaccine may also include polynucleotides encoding peptides known to stimulate an immune response, such as the CD154 polypeptide described herein.

The following examples are meant only to be illustrative and are not meant as limitations on the scope of the invention or of the appended claims.

EXAMPLES

Example 1. Construction of TRAP and TRAP/CD154 Inserts

Strains and Culture Conditions

All plasmids were first maintained in TOP10 *E. coli* cells (Invitrogen, Carlsbad, Calif., USA) unless described otherwise. *Salmonella* enteritidis 13A was used for introduction of mutations. *Salmonella enteritidis* strain 13A was a field isolate available from USDA/APHIS/NVSL and deposited with the ATCC as deposit number PTA-7871. Bacteria carrying plasmid pKD46 were grown at 30° C. Other bacteria were grown at 37° C. Plasmid curing was conducted at 37° C.

Luria-Bertani (LB) media was used for routine growth of cells, and SOC media (Invitrogen, Carlsbad, Calif., USA) was used for phenotypic expression after electroporation. When appropriate, the following antibiotics were added to the media: ampicillin (Amp) at 100 µg/ml, kanamycin (Km) at 50 µg/ml, and chloramphenicol (Cm) at 25 µg/ml.

Plasmids

Plasmids pKD46, pKD13, and pBC-I-SceI were described previously (Datsenko and Wanner, PNAS 2000, 97:6640-6645 and Kang et al., J Bacteriol 2004, 186:4921-4930, both of which are incorporated herein by reference in their entireties). Plasmid pKD46 encodes Red recombinase enzymes which mediate homologous recombination of incoming linear DNA with chromosomal DNA. This plasmid also contains the Ampicillin resistance gene and is temperature-sensitive so that it requires 30° C. for maintenance in the cell. Plasmid pKD13 served as a template for amplification of the Km resistance (Km$^r$) gene used in overlapping PCR. Plasmid pBC-I-SceI, which is maintained in the cell at 37° C., produces the I-SceI enzyme, which cleaves the following 18 base pair, rare recognition sequence: 5'-TAGGGATAACAGGGTAAT-3' (SEQ ID NO:16). Plasmid pBC-I-SceI also contains the chloramphenicol resistance (Cm$^r$) gene.

PCR

All primers used for PCR are listed in Table 1. Typically, PCR was performed using approximately 0.1 µg of purified genomic, plasmid or PCR-generated DNA (Qiagen, Valencia, Calif., USA), 1× cloned Pfu polymerase buffer, 5U Pfu polymerase (Stratagene La Jolla, Calif., USA), 1 mM dNTPs (GE Healthcare Bio-Sciences Corp., Piscataway, N.J.), and 1.2 µM of each primer in a total volume of 50 µL. The DNA engine thermal cycler (Bio-Rad, Hercules, Calif., USA) was used with the following amplification conditions: 94° C. for 2 minutes; 30 cycles of 94° C. sec for 30 sec, 58° C. for 60 sec, 72° C. for 90 sec per 1 kb; and 72° C. for 10 minutes for final extension. Each PCR product was gel purified (Qiagen, Valencia, Calif., USA) and either eluted in 25 µL EB buffer for preparation of templates used in overlapping extension PCR or in 50 µL EB buffer, ethanol precipitated and suspended in 5 µL of ddH$_2$O for electroporation into *S. enteritidis*.

TABLE 1

Primer sequences

| Primer | Amplified region | Primer sequence |
|---|---|---|
| lam-up-f | loop 9 up | 5'TGTACAAGTGGACGCCAATC 3' (SEQ ID NO: 17) |
| lam-up-r | | 5'*GTTATCGCCGTCTTTGATATAGCC* 3' (SEQ ID NO: 18) |
| lam-dn-f | loop 9 dn | 5'*ATTTCCCGTTATGCCGCAGC* 3' (SEQ ID NO: 19) |
| lam-dn-r | | 5'GTTAAACAGAGGGCGACGAG 3' (SEQ ID NO: 20) |
| Km-f | I-SceI/ Km$^r$ gene | 5'*GCTATATCAAAGACGGCGATAAC*TAAC TATAACGGTCCTAAGGTAGCGAATTTCCG GGGATCCGTCGA 3' (SEQ ID NO: 21) |
| Km-r | | 5'*GCTGCGGCATAACGGGAAATTGTAGGC* TGGAGCTGCTTCG 3' (SEQ ID NO: 22) |
| Kan4f | inside Km$^r$ gene: sequencing | 5'CAAAAGCGCTCTGAAGTTCC 3' (SEQ ID NO: 23) |
| Kan4r | | 5'GCGTGAGGGGATCTTGAAGT 3' (SEQ ID NO: 24) |
| SEQ1 hCD154 up reverse | SEQ1 hCD154/ loop 9 up | 5'GGAGGACGCAACCGCCGCGGTCGGAAA ACCACCACCGGAGGAGGA*GTTATCGCCGT CTTTGATATAGCC* 3' (SEQ ID NO: 25) |
| SEQ1hCD 154 down forward | SEQ1 hCD154/ loop 9 down | 5'CCGCGGCGGTTGCGTCCTCCTCCTGGG CAGAAAAAGGTTATTATACCATGTCTTCC TCCTC*CATTTCCCGTTATGCCGCAGC* 3' (SEQ ID NO: 26) |
| SEQ2 hCD154 up reverse | SEQ2- hCD154/ loop 9 up | 5'TTTTCTTCTTCTTCTTCCGGTTCCGGA CGTTCATGACCTTCTTCGGCTTTCGGCTG AACCGCCGGGGTTTCCGGCGCCGCGGAGG AGG*AGTTATCGCCGTCTTTGATATAGC C* 3' (SEQ ID NO: 27) |
| SEQ2 hCD154 up reverse | SEQ2- hCD154/ loop 9 down | 5'ACCGGAAGAAGAAGAAGAAAAAAAAGA AGAAGGTGGTGGTTTTCCGACCGCGGCGG TTGCGTCCTCCTCCTGGGCAGAAAAAGGT TATTATACCATGTCTTCCTCCTCC*ATTTC CCGTTATGCCGCAGC* 3' (SEQ ID NO: 28) |
| SEQ3 Hcd154 up reverse | SEQ3 hCD154/ loop 9 up | 5'GCAACACCACCACCAACCGCCGCGATC AGCAGAACACCACCAACACCACCCGCAAC CGCCGCGGTCGGAAAACCACCACCGGAGG *AGGAGTTATCGCCGTCTTTGATATAGC C* 3' (SEQ ID NO: 29) |

TABLE 1-continued

Primer sequences

| Primer | Amplified region | Primer sequence |
|---|---|---|
| SEQ3 hCD154 up reverse | SEQ3-hCD154/ loop 9 down | 5'GGCGGTTGGTGGTGGTGTTGCGGCGTT TACCTCCGGTGGTGGTGGTGCGGGTGCGC AGGAATCCTCCTCCTGGGCAGAAAAAGGT TATTATACCATGTCTTCCTCCTCCATTTC CCGTTATGCCGCAGC 3' (SEQ ID NO: 30) |
| lam 3f | outer regions of loop 9: sequencing | 5'GCCATCTCGCTTGGTGATAA 3' (SEQ ID NO: 31) |
| lam 3r | | 5'CGCTGGTATTTTGCGGTACA 3' (SEQ ID NO: 32) |

In Table 1, italicized nucleotides are complementary to either side of the lamB gene loop 9 insertion site, which corresponds to nucleotide 1257 using *S. typhimurium* as an annotated reference genome. Bold font nucleotides represent the I-SceI recognition site in the Km-f primer.

Electroporation

Transformation of pKD46 into *S. enteritidis* was the first step carried out so that Red recombinase enzymes could be used for mediating recombination of subsequent mutations. Plasmid pKD46 was harvested from *E. coli* BW25113 (Datsenko and Wanner, PNAS 2000, 97:6640-6645) using a plasmid preparation kit (Qiagen Valencia, Calif., USA). Then 0.5 µL of pKD46 DNA was used for transformation into *S. enteritidis* 13A which had been prepared for electroporation. (Datsenko and Wanner, PNAS 2000, 97:6640-6645). Briefly, cells were inoculated into 10-15 mL of 2×YT broth and grown at 37° C. overnight. Then 100 µL of overnight culture was re-inoculated into 10 mL fresh 2×YT broth at 37° C. for 3-4 hours. Cells to be transformed with pKD46 plasmid were heated at 50° C. for 25 minutes to help inactivate host restriction. Cells were washed five times in ddH$_2$O water and resuspended in 60 µL of 10% glycerol. Cells were then pulsed at 2400-2450 kV for 1-6 ms, incubated in SOC for 2-3 hours at 30° C. and plated on LB media with appropriate antibiotics. *S. enteritidis* transformants with pKD46 were maintained at 30° C. When these transformants were prepared for additional electroporation reactions, all steps were the same except that 15% arabinose was added to induce Red recombinase enzymes one hour prior to washing, and cells did not undergo the 50° C. heat step.

Loop 9 Up-I-SceI Km'-Loop 9 Down Construct

Figure 2A:
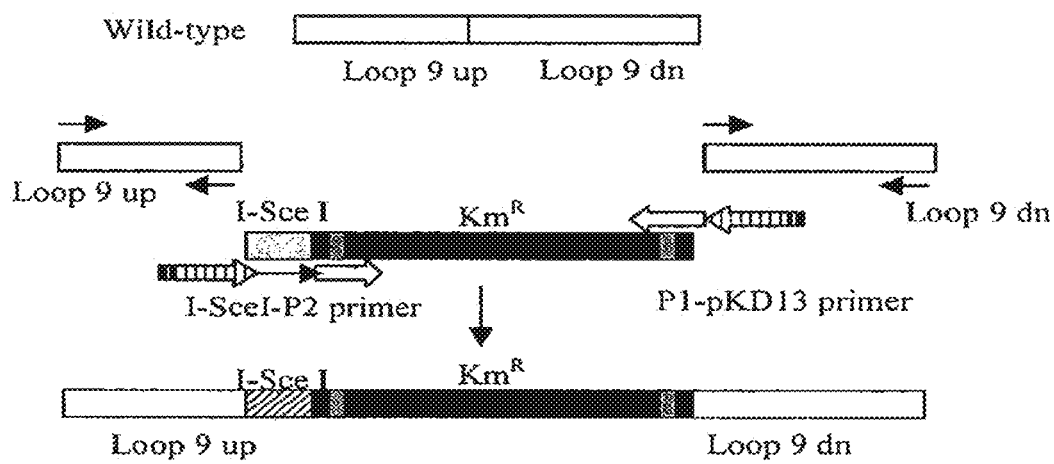
FIG. 2A and FIG. 2B depict the design scheme of the overlapping extension PCR method used to generate the TRAP and TRAP-CD154 insertions into loop 9 of the lamB polynucleotide.

Introduction of I-SceI enzyme recognition site along with the Km$^r$ gene into loop 9 of the lamB gene was done by combining the Red recombinase system (Datsenko and Wanner, PNAS 2000, 97:6640-6645, which is incorporated herein by reference in its entirety) and overlapping PCR (Horton et al., BioTechniques 1990, 8:528-535, which is incorporated herein by reference in its entirety). The insertion site corresponds to nucleotide 1257 of the lamB gene using *Salmonella typhimurium* LT2 (*S. typhimurium*) as an annotated reference genome. First, the upstream and downstream regions immediately flanking the loop 9 insertion site (loop 9 up and loop 9 down, respectively) were amplified separately. Primers used were lam-up-f and lam-up-r for loop 9 up and lam-dn-f and lam-dn-r for loop 9 down. Then the Km$^r$ gene from pKD13 plasmid was amplified using primers Km-f and Km-r. Here, the I-SceI enzyme site was synthetically added to the 5' end of Km-f primer then preceded by a region complimentary to the loop-up-r primer. Likewise, a region complimentary to the loop-dn-f primer was added to the 5' end of Km-r primer. The complimentary regions allow all 3 PCR products to anneal when used as templates in one PCR reaction. FIG. 2A represents this design scheme. PCR fragments consisting of loop 9 up-I-SceI/Km$^r$-loop 9 down sequence (PCR-A) were electroporated into *S. enteritidis* cells, which harbored pKD46 and were induced by arabinose, and then plated on LB with Km plates. To verify the correct sequence orientation of the mutation, we performed colony PCR with primer pairs Kan4F/lam3f and Kan4R/lam3r, where Kan4F and Kan4R are Km$^r$ gene-specific primers and lam3f and lam3r are primers located outside the lamB loop 9 region. These PCR fragments were gel purified (Qiagen, Valencia, Calif., USA) and used for DNA sequencing.

Loop 9 Up-TRAP-CD154-Loop 9 Down Construct

Figure 2B:
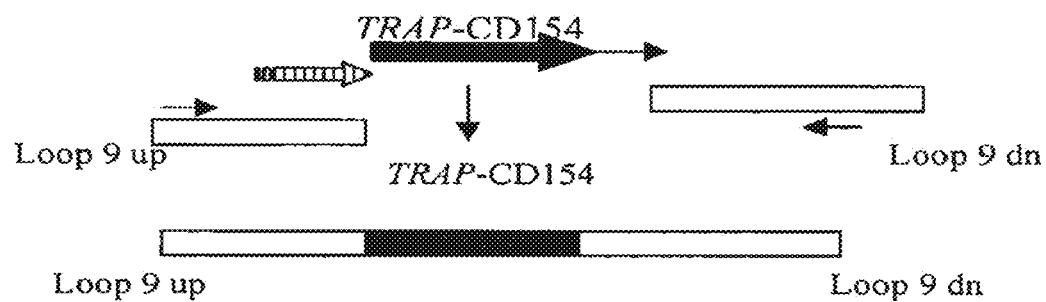
Figure 3:
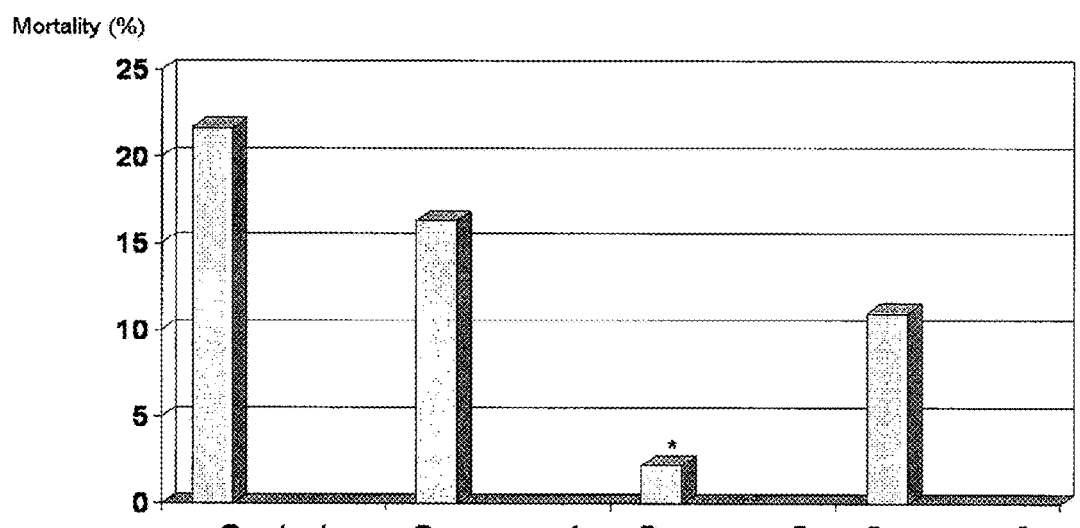
FIG. 3 is a bar graph showing the percent mortality at five days post-infection with *Eimeria* maxima after inoculation with a *Salmonella* vector expressing the indicated *Eimeria* TRAP sequence.

The final overlapping PCR fragment, PCR-B, contained the added TRAP antigen in combination with CD154 sequences flanked by loop 9 up and down regions (FIG. 2B). Combination sequences consisted of TRAP polynucleotide encoding SEQ ID NO:1-3 and CD154 along with spacers such as Serine (Ser) residues.

To shorten the amount of steps for construction of the next fragment, the TRAP-CD154 sequence was synthetically added to the 5' end of the lam-dn-f primer and preceded by the complimentary region to the loop-up-r primer. The previously used PCR product for loop 9 up could be used together with the newly constructed PCR product in which the TRAP-CD154s were incorporated at the 5' end of loop 9 down to perform the final PCR reaction. However, for other insert sequences, an extra PCR step was needed, due to the longer lengths of insert sequences, to amplify loop 9 up with added nucleotides specific to insertion sequences connected to loop-up-r primer. The coding sequence for Gly (GGT) and Serine (TCC) as well as all other amino acids were chosen based on compiled data of the most frequently used codons in *E. coli* and *Salmonella typhimurium* proteins. See Table 1 for further details of primer design.

I-SceI Site/$Km^r$ Insertion Mutation

The first mutation step involved designing a PCR fragment, PCR-A, which would serve as the carrier of the I-SceI site/$Km^r$ cassette to be inserted into the lamB site. PCR-A consisted of the I-SceI enzyme recognition site adjacent to the $Km^r$ gene with approximately 200-300 bp of flanking DNA on each end homologous to the upstream and downstream regions of lamB loop 9 insertion site (loop 9 up and loop 9 down, respectively). The fragment was introduced into *S. enteritidis* cells expressing Red recombinase enzymes and $Km^r$ colonies were selected. After screening a few colonies by colony PCR, positive clones were sequenced for the desired inserted I-SceI site/$Km^r$ sequence, and the identified mutant was selected and designated as SE164.

Genomic Replacement of I-SceI/$Km^r$ with TRAP-CD154s

The second mutation step required constructing a PCR fragment, referred to as PCR-B and shown in FIG. 2B, consisting of the final insertion sequence, the TRAP- CD154s, flanked by lamB homologous fragments. PCR-B amplicons have no selection marker and must be counter-selected after replacement for the previous I-SceI site/Km$^r$ mutation in SE164. Plasmid pBC-I-SceI encodes the Cm$^r$ gene and the I-SceI enzyme, which will cut the genome at the I-SceI site of SE164. Therefore, pBC-I-SceI was electroporated into SE164 along with PCR-B. After recombination of PCR-B to replace PCR-A, positive clones were chosen based on the ability to grow on Cm but not on Km. After DNA sequencing of mutants to confirm successful recombination of PCR-B, the strains were designated Sequence 1, Sequence 2 and Sequence 3. Ten random clones for each of the TRAP-CD154 insertions were used for PCR with lam 3f and lam 3r then digested using unique restriction enzymes sites for each insertion sequence and 100% of clones tested by digestion were positive for the desired mutation sequence. Sequencing results demonstrated that the insertion of TRAP-CD154 was exactly into the loop 9 region without the addition of extraneous nucleotides in each case. The inserts of the TRAP-CD154 vaccines are as follows: TRAP-CD154 (SEQ ID NO:33); TRAP-US-CD154 (SEQ ID NO:34); TRAP-DS-CD154 (SEQ ID NO:35).

Example 2. Attenuation of TRAP-CD154 Mutants/Inserts

Attenuation of SE13A was achieved by deletion mutation of the aroA gene and/or the htrA gene. Mutation of the aroA gene, a key gene in the chorismic acid pathway of bacteria, results in a severe metabolic deficiency which affects seven separate biochemical pathways. Mutation of the htrA gene reduces the cell's ability to withstand exposure to low and high temperatures, low pH, and oxidative and DNA damaging agents and reduces the bacteria's virulence.

To achieve deletion mutations in SE13A, the target gene sequence in the bacterial genome of *S. enteritidis* was replaced with the Km resistant gene sequence. This was completed using overlapping extension PCR and electroporation of the PCR products as described above. The Km resistance gene was targeted into the genomic region containing the genes of interest (aroA or htrA) by flanking the Km resistance gene with 200-300 base pairs of sequences homologous to the genes of interest. Once Km resistant mutants were obtained, the aroA and htrA deletion mutations were confirmed by DNA sequencing. Analogous aroA- and htrA-*Salmonella* strains were deposited with the American Type Culture Collection on Sep. 13, 2006 (Deposit No. PTA-7872 and Deposit No. PTA-7873, respectively). The attenuated strains were previously tested in vivo with regards to clearance time. Both of the attenuated strains had quicker clearance times than did the wildtype 13A strain, but both were able to colonize the liver, spleen, and cecal tonsils of chickens after oral infection. Attenuated strains comprising the TRAP-CD154s and lacking both aroA and htrA were isolated.

Example 3. Protection of Chicks from Mortality after *Eimeria* Infection

Day-of-hatch chicks (n=280) were orally vaccinated with about $1\times10^8$ cfu of the *Salmonella* isolates comprising the three distinct polynucleotides encoding the TRAP polypeptides of SEQ ID NO:1-3 or saline control. At 21 days of age, the chicks were orally challenged with $10^4$ sporulated oocysts of *Eimeria* maxima. The chicks were monitored daily post challenge. As depicted in FIG. 3, mortality of chicks at day 5 post challenge was reduced as compared to non-vaccinated animals irrespective of the vaccine strain given. The mortality was as follows: TRAP (SEQ ID NO:1) 7/43 (16.3%); TRAP US(SEQ ID NO:2) 1/46 (2.2.%); TRAP DS (SEQ ID NO:3) 6/43 (11%); Control (unvaccinated) 10/46 (21.7%). Surprisingly, the chicks vaccinated with a *Salmonella* comprising TRAP polypeptide of SEQ ID NO:2 demonstrated marked and significantly reduced mortality as compared to control non-vaccinated chicks ($P<0.001$). Necropsy was performed and indicated that all mortality was related to the *Eimeria* maxima infection.

In a repeat experiment, mortality in the vaccinated bird (6/48) was significantly lower than the controls (17/50) and performance was better in the vaccinated chicks, but the difference was not significant.

In addition, serum was collected from immunized birds and an ELISA for TRAP performed. A robust TRAP specific antibody response was generated in the birds vaccinated with TRAP-US (SEQ ID NO:2).

Example 4. Morbidity Associated with Vaccination is Limited

To evaluate the efficacy of TRAP US-CD154 (SEQ ID NO:34) as a potential vaccine candidate, a similar study was completed to investigate morbidity associated with vaccination. Broiler chickens were orally vaccinated with $1\times10^8$ cfu/bird of the *Salmonella* vaccine with TRAP US and CD154 insert (SEQ ID NO:34) or sham vaccinated with saline. Coccidia challenge was performed with sporulated oocytes of *Eimeria* maxima ($10^5$ sporulated oocysts/bird) at three weeks post-vaccination. Body weight gain and lesions were evaluated 7 days post-challenge. Immunized birds showed a significant ($p<0.01$) improvement in performance Immunized birds had about a 31% weight gain as compared to unvaccinated controls. Thus, vaccination with a *Salmonella*-based vaccine comprising a TRAP polypeptide and a CD154 polypeptide capable of binding CD40 may protect birds from morbidity and mortality associated with *Eimeria* infection.

We claim:

1. A vaccine comprising a vector comprising a first polynucleotide sequence encoding a thrombospondin-related anonymous protein (TRAP) polypeptide consisting of SEQ ID NO: 1, SEQ ID NO: 2 or SEQ ID NO: 3 or a fragment thereof comprising at least six consecutive amino acids of SEQ ID NO: 1, SEQ ID NO: 2 or SEQ ID NO: 3, wherein the polypeptide is expressed on a surface of the vector.

2. The vaccine of claim 1, further comprising a second polynucleotide sequence encoding a CD154 polypeptide capable of binding $CD_{40}$, the CD154 polypeptide having fewer than 50 amino acids and comprising amino acids 140-149 of SEQ ID NO:4 or is selected from the group consisting of SEQ ID NO:5, SEQ ID NO:6, SEQ ID NO:7, SEQ ID NO:8, and SEQ ID NO:9.

3. The vaccine of claim 2, wherein the vaccine comprises more than one copy of the second polynucleotide sequence.

4. The vaccine of claim 2, wherein the first polynucleotide sequence is linked in frame to the second polynucleotide sequence.

5. The vaccine of claim 1, wherein the vector is selected from the group consisting of a virus, a bacterium, and a liposome.

6. The vaccine of claim 5, wherein the vector is a bacterium.

7. The vaccine of claim 6, wherein the bacterium is selected from the group consisting of *Salmonella* species, *Bacillus* species, *Escherichia* species, and *Lactobacillus* species.

8. The vaccine of claim 6, wherein the first polynucleotide is inserted into a polynucleotide sequence encoding an external portion of a transmembrane protein.

9. The vaccine of claim 1, wherein the vaccine comprises more than one copy of the first polynucleotide sequence.

10. A method of inducing an immune response against an Apicomplexan parasite in a subject comprising administering to the subject the vaccine of claim 1 in an amount effective to induce the immune response of the subject to the Apicomplexan parasite.

11. The method of claim 10, wherein the vector is selected from the group consisting of a virus and a bacterium.

12. The method of claim 10, the vaccine further comprising a second polynucleotide sequence encoding a CD154 polypeptide capable of binding CD40, the CD154 polypeptide having fewer than 50 amino acids and comprising amino acids 140-149 of SEQ ID NO:4 or is selected from the group consisting of SEQ ID NO:5, SEQ ID NO:6, SEQ ID NO:7, SEQ ID NO:8, and SEQ ID NO:9.

13. The method of claim 12, wherein the first polynucleotide sequence is linked in frame to the second polynucleotide sequence.

14. The method of claim 10, wherein the vaccine is selected from the group consisting of *Salmonella* species, *Bacillus* species, *Escherichia* species, and *Lactobacillus* species.

15. The method of claim 10, wherein the first polynucleotide is inserted into a polynucleotide sequence encoding an external portion of a transmembrane protein.

16. The method of claim 10, wherein the vaccine comprises more than one copy of the first polynucleotide sequence.

17. The method of claim 10, wherein the vaccine is administered by a method selected from the group consisting of oral, intranasal, parenteral, and in ovo.

18. The method of claim 10, wherein the immune response comprises an enhanced antibody response or an enhanced T cell response.

19. The method of claim 10, wherein the subject is member of a poultry species or is a mammal.

20. The method of claim 10, wherein the vaccine is killed prior to administration to the subject or is not capable of replicating in the subject.

21. The method of claim 10, wherein the Apicomplexan parasite is selected from the group consisting of *Eimeria, Plasmodium, Toxoplasma*, and *Cryptosporidium*.

22. A method of reducing morbidity associated with infection with an Apicomplexan parasite in a subject comprising administering to the subject the vaccine of claim 1 in an amount effective to enhance the immune response of the subject to the Apicomplexan parasite.

* * * * *